(12) United States Patent
Bonacorsi et al.

(10) Patent No.: US 8,735,069 B2
(45) Date of Patent: May 27, 2014

(54) **METHOD FOR DETECTING MICROORGANISMS OF *KINGELLA* GENUS**

(75) Inventors: Stéphane Bonacorsi, Nogent sur Marne (FR); Philippe Bidet, Vincennes (FR); Edouard Bingen, Paris (FR)

(73) Assignees: Assistance Publique—Hôpitaux de Paris, Paris (FR); Université Paris Diderot-Paris 7, Paris (FR)

( * ) Notice: Subject to any disclaimer, the term of this patent is extended or adjusted under 35 U.S.C. 154(b) by 357 days.

(21) Appl. No.: 13/119,851

(22) PCT Filed: Sep. 18, 2009

(86) PCT No.: PCT/EP2009/062142
§ 371 (c)(1),
(2), (4) Date: Jun. 10, 2011

(87) PCT Pub. No.: WO2010/031851
PCT Pub. Date: Mar. 25, 2010

(65) Prior Publication Data
US 2011/0229900 A1 Sep. 22, 2011

(30) Foreign Application Priority Data

Sep. 19, 2008 (EP) .................................. 08164748
Jun. 19, 2009 (EP) .................................. 09163319

(51) Int. Cl.
*C12Q 1/68* (2006.01)
*C12P 19/34* (2006.01)

(52) U.S. Cl.
USPC .......................... 435/6.12; 435/6.1; 435/6.11

(58) Field of Classification Search
None
See application file for complete search history.

(56) References Cited

PUBLICATIONS

Lin Yin et al., "Real-time reverse transcriptase-polymerase chain reaction (RT-PCR) for measurement of cytokine and growth factor mRNA expression with fluorogenic probes of SYBR Green I," Immunology and Cell Biology, 2001, vol. 79, pp. 213-221.*
Lee et al., "Acute *Kingella kingae* Endocarditis with Recurrent Cerebral Emboli in a Child with Mitral Prolapse," Annals of Neurology, 2004, vol. 16, No. 1, pp. 88-89.*
Birgisson H, Steingrimsson O and Gudnason T. *Kingella kingae* infections in paediatric patients: 5 cases of septic arthritis, osteomyelitis and bacteraemia. Scand J Infect Dis 1997;29:495-8.
Bonacorsi S, Farnoux C, Bidet P, et al. Treatment failure of nosocomial pertussis infection in a very-low-birth-weight neonate. J Clin Microbiol 2006;44:3830-2.
Chometon S, Benito Y, Chaker M, et al. Specific real-time polymerase chain reaction places *Kingella kingae* as the most common cause of osteoarticular infections in young children. Pediatr Infect Dis J 2007;26:377-81.
Dagan R, Shriker O, Hazan I, et al. Prospective study to determine clinical relevance of detection of pneumococcal DNA in sera of children by PCR. J Clin Microbiol 1998;36:669-73.
Gene A, Garcia-Garcia JJ, Sala P, Sierra M and Huguet R. Enhanced culture detection of *Kingella kingae*, a pathogen of increasing clinical importance in pediatrics. Pediatr Infect Dis J 2004;23:886-8.
Kehl-Fie TE, St Geme JW, 3rd. Identification and characterization of an RTX toxin in the emerging pathogen *Kingella kingae*. J Bacteriol 2007;189:430-6.
Kiang KM, Ogunmodede F, Juni BA, et al. Outbreak of osteomyelitis/septic arthritis caused by *Kingella kingae* among child care center attendees. Pediatrics 2005;116:e206-13.
Kugler KC, Biedenbach DJ and Jones RN. Determination of the antimicrobial activity of 29 clinically important compounds tested against fastidious HACEK group organisms. Diagn Microbiol Infect Dis 1999;34:73-6.
Lebel E, Rudensky B, Karasik M, Itzchaki M and Schlesinger Y. *Kingella kingae* infections in children. J Pediatr Orthop B 2006;15:289-92.
Luhmann JD, Luhmann SJ. Etiology of septic arthritis in children: an update for the 1990s. Pediatr Emerg Care 1999;15:40-2.
Lundy DW, Kehl DK. Increasing prevalence of *Kingella kingae* in osteoarticular infections in young children. J Pediatr Orthop 1998;18:262-7.
Maas KS, Mendez M, Zavaleta M, et al. Evaluation of brucellosis by PCR and persistence after treatment in patients returning to the hospital for follow-up. Am J Trop Med Hyg 2007;76:698-702.
Moumile K, Merckx J, Glorion C, Berche P and Ferroni A. Osteoarticular infections caused by *Kingella kingae* in children: contribution of polymerase chain reaction to the microbiologic diagnosis. Pediatr Infect Dis J 2003;22:837-9.
Nilsson AC, Bjorkman P and Persson K. Polymerase chain reaction is superior to serology for the diagnosis of acute *Mycoplasma pneumoniae* infection and reveals a high rate of persistent infection. BMC Microbiol 2008;8:93.
Rosey AL, Abachin E, Quesnes G, et al. Development of a broad-range 16S rDNA real-time PCR for the diagnosis of septic arthritis in children. J Microbiol Methods 2007;68:88-93.
Ross JJ, Saltzman CL, Carling P and Shapiro DS. Pneumococcal septic arthritis: review of 190 cases. Clin Infect Dis 2003;36:319-27.
van der Heijden IM, Wilbrink B, Vije AE, Schouls LM, Breedveld FC and Tak PP. Detection of bacterial DNA in serial synovial samples obtained during antibiotic treatment from patients with septic arthritis. Arthritis Rheum 1999;42:2198-2203.
Verdier I, Gayet-Ageron A, Ploton C, et al. Contribution of a broad range polymerase chain reaction to the diagnosis of osteoarticular infections caused by *Kingella kingae*: description of twenty-four recent pediatric diagnoses. Pediatr Infect Dis J 2005;24:692-6.
Wang CL, Wang SM, Yang YJ, Tsai CH and Liu CC. Septic arthritis in children: relationship of causative pathogens, complications, and outcome. J Microbiol Immunol Infect 2003;36:41-6.
Yagupsky P, Dagan R, Howard CW, Einhorn M, Kassis I and Simu A. High prevalence of *Kingella kingae* in joint fluid from children with septic arthritis revealed by the BACTEC blood culture system. J Clin Microbiol 1992;30:1278-81.
Yagupsky P, Dagan R, Prajgrod F and Merires M. Respiratory carriage of *Kingella kingae* among healthy children. Pediatr Infect Dis J 1995;14:673-8.

(Continued)

*Primary Examiner* — Young J Kim
(74) *Attorney, Agent, or Firm* — Novak Druce Connolly Bove + Quigg LLP

(57) ABSTRACT

The invention relates to a method for detecting *Kingella* microorganisms through PCR of a chaperonin gene.

9 Claims, 1 Drawing Sheet

(56) References Cited

PUBLICATIONS

Yagupsky P, Dagan R. *Kingella kingae*: an emerging cause of invasive infections in young children. Clin Infect Dis 1997;24:860-6.

Yagupsky P, Katz O and Peled N. Antibiotic susceptibility of *Kingella kingae* isolates from respiratory carriers and patients with invasive infections. J Antimicrob Chemother 2001;47:191-3.

Yagupsky P. Diagnosis of *Kingella kingae* arthritis by polymerase chain reaction analysis. Clin Infect Dis 1999;29:704.

Yagupsky P. *Kingella kingae*: from medical rarity to an emerging paediatric pathogen. Lancet Infect Dis 2004;4:358-67.

"*Kingella kingae* strain ATCC 23330 Cpn60 (cpn60) gene, partial cds.", Database: EMBL, Accession No. AY123650, Aug. 9, 2002.

Chometon, S., et al., "Specific real-time polymerase chain reaction places *Kingella kingae* as the most common cause of osteoarticular infections in young children," The Pediatric Infectious Disease Journal, vol. 26, No. 5, pp. 377-381, May 2007.

Ilharreborde, B.,et al., "New real-time PCR-based method for *Kingella kingae* DNA detection: application to samples collected from 89 children with acute arthritis," Journal of Clinical Microbiology, vol. 47, No. 6, pp. 1837-1841, Jun. 2009.

Rosey, A.-L., et al., "Development of broad-range 16S rDNA real-time PCR for the diagnosis of septic arthritis in children," Journal of Microbiological Methods, 2007, vol. 68, pp. 88-93.

Verdier, I. et al., "Contribution of a broad range polymerase chain reaction to the diagnosis of osteoarticular infections caused by *Kingella kingae*," The Pediatric Infectious Disease Journal, vol. 24, No. 8, pp. 692-696, Aug. 2005.

* cited by examiner

```
1 : AY123650  : K. kingae strain ATCC 23330
2 : EU864312  : K. kingae strain ATCC 23331
3 : EU864313  : K. kingae strain CIP 73.1
4 : EU864314  : K. kingae strain CIP 102473
5 : EU864315  : sample 80700158; knee arthritis in a 16 months old girl, Paris, France
6 : EU864316  : sample 80900052; ankle arthritis in a 13 months old boy, Paris, France
7 : Consensus sequence of K. kingae reference strains ----+---10   ----+---20   ----+---30   ----+---40   ----+---50   ----+---60   ----+---70   ----+---80   ----+---90   ----+--100
1  GCAAGAAGTC GGCAAAGAGG GCGTGATTAC CGTTGAAGGC GGCAAATCAT TGGAAAACGA GTTAGAAGTG GTTAAAGTA TGCAATTTGA CCGTGGCTAC
2  .......... .......... .......T. .C.....AA. .......... .......... .......G.. .......... .......... ..........
3  .......... .......... .......... .......... .......... .......... .......G.. .......... .......... .......C..
4  .......... .......... .......... .....A.... .......... .......... .......G.. .......... .......... ..........
5  .......... .......... .......... .....A.... .......... .......... .......G.. .......... .......... ..........
6  .......... .......... .......... .....A.... .......... .......... .......G.. .......... .......... ..........
7  GCAAGAAGTC GGCAAAGAGG GCGTGATT.C C.TTGAA..C GGCAAATCAT TGGAAAACGA GTT.GAAGTG GTTAAAGTA TGCAATTTGA CCG.GGCTAC
   >  forward primer  >                                                             <  probe hybridization zone   <

----+--110   ----+--120   ----+--130   ----+--140   ----+--150   ----+--160   ----+--170   ----+--180   ----+--190   ----+--200
1  TTGTCGGCCTT ATTTCGTGAA TGATTTGGAA AAACAAATCG CTGGTTTGGA CAGCCCATTT GTGTTGTTGT TTGAC
2  .......... .......... .......... .......... .......... .......... .......... .....
3  ...A...... ......T... .......... .......... .......... .......... .......... .....
4  .......... .......... .......... .......... .......... .......... .......... .....
5  .......... .......... .......... .......... ---------- ---------- ---------- -----
6  .......... .......... .......... .......... ---------- ---------- ---------- -----
7  TTGTC.CCTT ATTT.GTGAA TGATTTGGAA AAACAAATCG CTGGTTTGGA CAGCCCATTT GTGTTGTTGT TTGAC
                                                              <   reverse primer   <
```

METHOD FOR DETECTING MICROORGANISMS OF *KINGELLA* GENUS

RELATED APPLICATIONS

This application is a national stage application (under 35 U.S.C. §371) of PCT/EP2009/062142, filed Sep. 18, 2009, which claims benefit of European applications 08164748.9, filed Sep. 19, 2008 and 09163319.8, filed Jun. 19, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 15351_6_US_Sequence_Listing. The size of the text file is 5 KB, and the text file was created on Mar. 17, 2011.

Acute septic arthritis in children must be diagnosed and treated urgently because of the risk of long-term sequelae. Identification of the causative organism is required to optimize the choice of antibiotics, but cultures are negative in one-third to two-thirds of patients [1-3]. *Kingella kingae*, a Gram-negative coccobacillus, is part of the normal oropharyngeal flora of young children from 6 months to 4 years [4, 5]. It was initially considered as a rare cause of invasive diseases, including skeletal infections in children and endocarditis in adults. However, the reported number of cases of *K. kingae* arthritis has increased markedly since the 1990s, mainly owing to improvements in culture techniques, such as inoculation of blood culture vials with joint specimens [3, 6]. In the literature, *K. kingae* currently accounts for 5% to 29% [2, 7-9] of culture-positive osteoarticular infections (OAI), and for up to 48% of cases of septic arthritis in children under 2 years of age [10].

*K. kingae* is a fastidious microorganism and its frequency in OAI may still be underestimated. Indeed, several molecular methods have recently shown a higher prevalence of *K. kingae* than previously reported in this setting. Rosey et al. and Verdier et al, using a universal 16S ribosomal DNA PCR method, found *K. kingae* sequences in respectively 18% and 14% of culture-negative specimens from infants with OAI [2, 9]. Recently, Chometon et al., using a nonprobed real-time PCR method, found that *K. kingae* was the leading cause of OAI in children in Lyon (France) [7].

Detection of bacterial DNA does not provide irrefutable proof that the relevant bacterium has a pathogenic role [11]. Indeed, Dagan et al have shown that the DNA of organisms colonizing the respiratory tract, such as pneumococci, can be detected by PCR in serum of uninfected patients [12]. Thus, given the ability of *K. kingae* to colonize the respiratory tract of young children [5], a suitable control is needed to confirm the relevance of PCR-based diagnoses.

Contrary to culture, molecular methods can detect a pathogen for up to several days or weeks after the outset of effective antibiotic therapy in various infectious diseases [13-16]. In this respect it would be of interest to determine the contribution of PCR to diagnose *K. kingae* infection in children who have already received antibiotics before joint fluid aspiration.

The present invention describes and evaluates a new *K. kingae*-specific real-time PCR method with a fluorogenic probe, and applies it to blood and joint fluid samples from children with suspected acute septic arthritis. The characteristics of *K. kingae* arthritis in this age group are also described.

The invention thus relates to a method for detecting the presence of a microorganism of *Kingella* genus in a biological sample of a patient, comprising the PCR amplification of all or part of a chaperonin gene of said microorganism.

Chaperonins or chaperones are proteins that assist the non-covalent folding/unfolding and the assembly/disassembly of other macromolecular structures, but do not occur in these structures when the latter are performing their normal biological functions. They are often concerned with protein folding, but also assist the assembly of other structures such as nucleosomes from folded histones and DNA. Some assembly chaperones, especially in the nucleus are concerned with the assembly of folded subunits into oligomeric structures.

The amino-acid structure of chaperonins is quite conserved among species. As an example, there is some identity between cpn60 of *K. kingae* and the orthologuous protein in *Neisseria*.

In order to identify chaperonin proteins in *Kingella*, it is possible to design a probe from a conserved region of a chaperonin from other microorganisms, and to use this probe on the genome of *Kingella*. Said genome has preferably been cut and cloned in vectors, such as BAC or cosmids. Hybridization of the probe to one (or more) of the vectors indicates the presence of a gene presenting homology with this probe in said vector. It is thus possible to sequence the vector, identify the gene and confirm that it codes for a chaperonin protein. Said method (and others) are well known to the person skilled in the art.

Alternatively, it is possible to sequence the whole genome of a *Kingella* microorganism. Sequencing a full bacterial genome is now well described in the art. It is then possible to predict the coding sequences in this genome, using specific software (this is also easier to do so in bacterial genomic sequence than in eukaryotic genomic sequences, due to the absence of introns). Comparison of the predicted proteins with databases will lead to identification of the chaperonin proteins of the *Kingella* genome.

In the preferred embodiment, said chaperonin gene is a cpn60, a partial sequence of which being represented by SEQ ID NO: 1. SEQ ID NO: 1 corresponds to the sequence GenBank AY123650. Cpn 60 corresponds probably to GroEL in *Escherichia coli*.

The GroEL proteins family is well described in the art. Brocchieri and Karlin (Protein Science, 2000, 9:476-86) have described the conservation among Hsp60 (another name of GroEL) sequences in relation to structure, function and evolution. The peptide obtained from translating SEQ ID NO: 1 presents amino acids that are specific of a GroEL protein. Using these sequences homology, it is thus easy to identify cpn60 proteins from *Kingella*.

The inventors have identified a sequence in this protein, conserved among various biological strains, and determined specific primers and probes that can be used to detect the presence of said gene in a sample from a patient. Presence of this gene amounts to the presence of the host, namely the *Kingella* microorganism.

In particular, said conserved sequence comprises nucleotides 225 to 399 of SEQ ID NO: 1, and may be amplified with a pair of primers chosen among (SEQ ID NO: 2/SEQ ID NO: 3) and (SEQ ID NO: 4/SEQ ID NO: 5). It is preferred to use SEQ ID NO: 2/SEQ ID NO: 3, in particular for specific detection of *K. kingae*.

Such amplified nucleic acids comprise the sequences depicted from SEQ ID NO: 11 to SEQ ID NO: 16. These six sequences correspond to amplified products from reference strains and from strains isolated from patients.

The method of the invention makes it possible to detect the presence of microorganisms of *Kingella* genus, and in particular *Kingella kingae*.

The biological sample on which the amplification is performed is any biological sample (in particular blood, urine, cerebrospinal fluid, endocardic tissue or bone sample). Nevertheless, due to the nature of the sought microorganism, the method is advantageously performed on a joint fluid sample.

The method of the invention is performed on a biological sample that has previously been harvested from a patient, by any method known in the art. In a preferred embodiment, said patient is a child less than 15 years old. Indeed, *Kingella* infections are more often present on children. In another embodiment, said patient is a child less than 5 years old.

The method of the invention is interesting to assess or confirm a diagnostic of a *Kingella* infection in a patient who has acute arthritis, osteomyelitis or endocarditis.

The amplification is performed according to methods known in the art. U.S. Pat Nos. 4,683,202, 4,683,195, 4,800,159, and 4,965,188 disclose conventional PCR techniques. PCR typically employs two oligonucleotide primers that bind to a selected nucleic acid template (e.g., DNA or RNA) denaturated by heating. A thermostable polymerase catalyzes the formation of primer extension products complementary to the template.

Real Time quantitative PCR (qPCR) makes it possible to determine the quantity of a specific DNA in a sample. It may be performed directly on a RNA template (where Reverse Transcription is performed before amplification), or from cDNA (Reverse Transcription being performed in a separate tube). It is also easily performed directly on bacterial genomic DNA.

The quantification of the starting nucleic acid is basically performed by using labeled primers or moieties that will bind to the double stranded nucleic acids obtained at each cycle of amplification. These labelled moieties, once linked to the DNA will emit a detectable signal (generally fluorescence) that is proportional to the quantity of double stranded DNA et can be measured in real time directly in the reaction tube between two cycles of amplification.

An important parameter for qPCR is the Ct value, which is the cycle where there is a significant increase in reporter signal. This value is related to the initial amount of DNA and the lower the Ct value, the higher the sensitivity of the assay. For cycles after Ct, there is an exponential increase of detected fluorescence (linked to the exponential increase of amplified DNA), until the amplified DNA reaches a plateau.

SYBR® Green I is a very commonly used reagent for qPCR. It is a dye that non-specifically intercalates in double stranded DNA (dsDNA). The amount of dye intercalated is proportional to the amount of double stranded DNA.

Another possibility is to use TaqMan® probes. A fluorophore is attached to the 5' end of the probe and a quencher to the 3' end. Said quencher may be a fluorophore emitting fluorescence by FRET (Fluorescence Resonance Energy Transfer) when excited by the energy (wavelength) emitted by the first fluorophore upon excitation by the machine. Examples of such couples of fluorophores/quencher is the couple FAM/TAMRA.

Said quencher may also be a "black-hole" (or dark) quencher, which absorbs the energy emitted by the fluorophore, but releases it as heat rather than fluorescence, thus leading to a better signal to noise ratio.

The principle of TaqMan® probes is identical, whatever the quencher used. The probe binds to the amplicon during each annealing step of the PCR. When the Taq polymerase extends from the primer which is bound to the amplicon, it displaces the 5' end of the probe, which is then degraded by the 5'-3' exonuclease activity of the Taq polymerase. Cleavage continues until the remaining probe melts off the amplicon. This process releases the fluorophore and quencher into solution, spatially separating them (compared to when they were held together by the probe).

In the case a couple of fluorophores (such as FAM/TAMRA) is used, this leads to an irreversible increase in fluorescence from the first fluorophore (FAM) and a decrease in the fluorescence of the quencher (TAMRA). When using a black-hole quencher, one can observe an irreversible increase in fluorescence from the fluorophore.

Dark quenchers are completely non-fluorescent, and have an extremely low background. Using dark quenchers significantly improves signal to noise ratios and thus give a higher sensitivity in multiplex PCR.

It is also possible to use molecular beacons probes. These are well known in the art, and are single-stranded oligonucleotide hybridization probes that form a stem-and-loop structure, where the loop contains the probe sequence complementary to the target sequence, and the stem is formed by the annealing of complementary arm sequences that are located on either side of the probe sequence. A fluorophore is covalently linked to the end of one arm and a quencher is covalently linked to the end of the other arm, so that the the fluorophore is very close to the nonfluorescent quencher when the molecular beacons are free in solution. There is thus no fluorescence emission.

When the molecular beacons hybridize to a nucleic acid strand containing a target sequence, they form a probe-target hybrid that is longer and more stable than the stem hybrid, thereby undergoing a spontaneous conformational reorganization that forces the stem hybrid to dissociate. The fluorophore and the quencher move away from each other, thus restoring fluorescence.

It is also possible to use probes that possess both advantages of TagMan® and molecular beacons probes. These probes are complementary to the target sequences and a "tail" (a few nucleotides) is added at their 3' end that is complementary to the first nucleotides of the probe. A fluorophore is covalently linked to the end of one arm of the probe and a quencher is covalently linked to the end of the other arm. When the probe is free in solution, it forms a loop as the molecular beacons, thereby leading to no fluorescence. When the target sequence is present, the probe hybridizes to it, thereby leading to restoration of the fluorescence. Since the 5'end of the probe is complementary of the target sequence, the Taq polymerase (extending from the primer which is bound to the amplicon) will be able to the 5' end of the probe and degrade it (as occurs in TagMan®), thereby releasing the fluorophore. There are thus two sources of fluorescence emission during amplification (binding of the probe to the amplified targets and release of the fluorophore), thereby increasing the sensibility of detection.

Use of real-time PCR makes it possible to detect the presence of a specific DNA in a sample more quickly and more easily than conventional PCR.

The invention also relates to a kit for detecting a microorganism of *Kingella* genus (especially *K. kingae*) comprising a pair of primers chosen among (SEQ ID NO: 2/SEQ ID NO: 3) and (SEQ ID NO: 4/SEQ ID NO: 5) and the probe of sequence SEQ ID NO: 7. Instructions for using this kit may also be included.

FIGURES

FIG. 1: Pretty alignment of cpn60 gene-amplification region sequences in *Kingella kingae* strains and positive samples (SEQ ID NO: 11 to SEQ ID NO: 16).

1st Sequence: reference sequence for *K. kingae* type strain.
2nd to 4th Sequences: other reference strains of *K. kingae*.
5th and 6th Sequence: cpn60 PCR performed directly on patients samples without positive culture.

In 2nd to 6th sequence, dots represent bases identical to 1St sequence.

In 7th sequence, dots represent non-consensus bases among the four *K. kingae* reference strains. The probe and primers hybridization regions are indicated in bold and underlined font on the consensus sequence (7th sequence, SEQ ID NO: 17).

EXAMPLES

Materials and Methods
Patients and Diagnosis

This study involved all children admitted to the hospital between January 2006 and January 2008 for suspected acute septic arthritis. This diagnosis was defined by joint pain and limited limb movement with or without fever (38° C.) and joint effusion visualized by radiography or sonography. All the children with suspected acute septic arthritis had fluoroscopically guided joint fluid aspiration to document the infection. Biological evaluation included the peripheral blood white cell count (WBC), the C-reactive protein (CRP) and fibrinogen levels.

Microbiological Methods

Before surgery, a blood sample was inoculated into aerobic blood culture vials (BacT/ALERT 3D, BioMérieux). During surgery, joint fluid was immediately inoculated into aerobic blood culture bottles. The remaining joint fluid sample was sent to the laboratory for Gram staining, cell count and for immediate inoculation onto Columbia blood agar (incubated in anaerobic conditions), chocolate agar (incubated in CO2-enriched air) and brain-heart broth. Aliquots (100-200 µl) were stored at −80° C. for DNA extraction. Blood culture bottles and the other media were incubated for respectively 5 and 10 days. When sufficient sample was available, 100 to 200 µl of plasma was separated from blood samples obtained for WBC counting or clotting tests, and was stored at −80° C. for DNA extraction. Joint fluid drainage samples were collected two, four and six days after surgery and stored at −80° C. for DNA extraction.

*K. kingae* identification was based on the microbiological characteristics [10]. Antibiotic susceptibility was tested with the disk diffusion method on Mueller-Hinton sheep blood agar in CO2-enriched air as previously described [17]. β-lactamase activity was detected with the nitrocefin test.

Preliminary Molecular Investigations

In order to develop a highly specific PCR-based diagnostic method for *K. kingae*, two primer pairs—Ksm1 (5'GCAAGAAGTCGGCAAAGAG 3', SEQ ID NO: 2) and Ksm2 (5' GTCAAACAACAACACAAATGGG 3', SEQ ID NO: 3), amplifying a 175-bp fragment, and KingF (TGTTGGCGCAAGCGATTGTTGCTG, SEQ ID NO: 4) and KingR (CGCCCACTTGAGCGATTTGCTCG, SEQ ID NO: 5), amplifying a 169-bp fragment—were first designed using the sequence of the nonribosomal gene cpn60, which was the only sequence available in the Public Database at the outset of the study (accession number AY123650). The specificity of the primers was assessed by conventional PCR on four reference strains of *K. kingae*, 12 genetically related species and genera, and four non-*K. kingae* isolates from patients with septic arthritis (Table 1). Amplification products obtained with the most specific primers were sequenced, yielding a consensus sequence and allowing us to design a specific "Kingprobe": FAM-CGCGATCGCGACAAGTAGCCACG-GTCAAGATCGCG-BHQ1 (SEQ ID NO: 6). A preferential Kingprobe sequence to use is 6-carboxyfluorescein-CGGTCAAATTGCATACCTTTAACCACTTCTTGACCG-black hole quencher 1 (SEQ ID NO: 7).

Molecular Diagnosis

Once a week, DNA was extracted from specimens with the BioRobot EZ1 workstation, using the EZ1 DNA Tissue Kit (Qiagen) according to the manufacturer's recommendations. Part of the DNA extract was immediately amplified, and the remainder was stored at −80° C. A negative extraction control was included in each run, consisting of all the reagents used for DNA extraction, minus the sample. The real-time PCR mixture contained 5 µL of DNA, 1 µL of each primer (Ksm1 and Ksm2) at 10 µM, 1 µL of probe at 10 µM, and 25 µL of IQ Multiplex Powermix (BioRad) in a final volume of 50 µL. Amplification was performed in an iCycler (BioRad) with an initial step of 15 minutes at 95° C., followed by 45 cycles of 15 seconds at 95° C., 30 seconds at 55° C., and 30 seconds at 72° C., and a final extension step of 10 minutes at 72° C. A positive control consisting of DNA extracted from *K. kingae* CIP8016 was included in each reaction. For each sample, amplification of the human betaglobulin gene (262 bp) with primers B2M-TR-1 (5' GCAAGGACTGGTCTTTCTATC 3', SEQ ID NO: 8) and B2M-TR-2 (5' TACACAACTTTCAG-CAGCTTACA 3', SEQ ID NO: 9) and the probe B2M-TR-sde (FAM-CGTGCCCTGCCGTGTGAACCATGT-GACTTTGGCACG-BHQ1, SEQ ID NO: 10) served as an internal positive extraction control and to detect the presence of PCR inhibitors.

Treatment

If purulent fluid was recovered from joint fluid aspiration open arthrotomy or arthroscopy was performed for joint lavage. After surgery, all the patients received a standardized treatment protocol. Empirical antibiotic therapy was started with intravenous cefotaxime (200 mg/kg/24 h) and fosfomycin (200 mg/kg/24 h) for 7 days, followed in case of no documented arthritis, by oral amoxicillin/clavulanic acid (80 mg/kg/24 h) and rifampin (20 mg/kg/24 h) for 5 weeks. In case of documented *K. kingae* arthritis, the antibiotic regimen consisted of amoxicillin alone (150 mg/kg/24 h in 3 fractions), for the same length of time. Cast immobilization was not used. All the patients had a minimum of 6 months of follow-up.

Statistical Analysis

Means and frequencies were compared using the Mann-Whitney U-test and the Chi-2 test. P values below 0.05 were considered to denote significant differences.

Results
Development of real-time *K. kingae*-specific PCR

Of the two primer pairs, only Ksm1-Ksm2 was highly specific for *K. kingae* (Table 1). This pair was used to obtain partial cpn60 gene sequences from four *K. kingae* reference strains and from two of our clinical isolates. The resulting sequences, excluding regions that we found contained several point mutations (n=8) (accession numbers: EU864312-EU864316), were then used to design a probe (FIG. 1). The RT PCR results for the panel of test strains were in perfect agreement with the results of conventional PCR. The detection limit of the RT PCR method, determined with serial dilutions of *K. kingae* genomic DNA containing $10^6$ copies to 1 copy number was 200 copies number.

Demographic and Microbial Characteristics

During the study period, 89 patients aged from 1 month to 14 years (mean: 45 months) underwent surgery in the hospital for suspected septic arthritis. None had received antibiotics in the week before their admission. A microorganism was cultured in 36 (40%) cases. *Staphylococcus aureus* was most prevalent (19 cases, 53%), followed by *K. kingae* (7 cases, 19%). The performance of the different culture methods for *K. kingae* isolation is indicated in table 2. *K. kingae* was never isolated by peripheral blood culture. None of the seven *K. kingae* isolates produced β-lactamases, and all were susceptible to amoxicillin, cefuroxime, cefotaxime, cotrimoxazole, ciprofloxacin and rifampicin. The other pathogens were Streptococcus pneumoniae (4 cases, 11%), Salmonella spp (3 cases, 8.3%), and non encapsulated *Haemophilus influenzae, Neisseria meningitidis* serogroup W135, and *E. coli* K1 in one case each.

Our specific RT PCR method was positive in all the patients with *K. kingae*-positive culture, and negative in all other patients with microbiologically documented arthritis. Among the 53 culture-negative patients, RT PCR assay identified *K. kingae* in 24 cases (45%). Thus, when culture and RT PCR were combined, *K. kingae* was the primary pathogen among the documented cases (31/(36+24); 52%), ahead of *S. aureus* (19/60; 32%). RT PCR was also applied to DNA extracts from blood samples of 15 patients with a molecular diagnosis of *K. kingae* infection (Table 2). None was positive. RT PCR was also applied to joint drainage fluid samples from 9 patients. All nine samples obtained 48 h after treatment initiation were positive. Four (80%) of the five samples obtained after four days were positive, and so were 3 (75%) of the 4 samples obtained after 6 days (Table 2).

Baseline Clinical and Biological Characteristics of Patients with *K. Kingae* Arthritis (Table 3)

Twenty-seven (87%) of the 31 children with *K. kingae* arthritis were less than 24 months old compared to only three (16%) of the 19 children with *S. aureus* arthritis (p<0.001). Symptoms started an average of 3 days before admission (range 1-10 d). The most frequently affected joint was the knee (52%), followed by the hip (26%). One-third of the patients were not febrile at admission. The CRP level was slightly elevated in all but one case. The fibrinogen level was elevated in all the patients tested. In contrast, the white blood cell count was abnormal in only three cases. Gram staining of joint fluid showed *K. kingae* in only one case. Joint fluids were hematic in 6 cases and purulent in others with a median cells count of 106,000 cells/mm$^3$ (range, 5,900-3,200,000 cells/mm$^3$). The seasonal distribution of *K. kingae* arthritis was as follows: 9 cases in fall, 7 cases in winter, 13 cases in spring, and 2 cases in summer.

Outcome

After 3 days of intravenous antibiotic therapy the CRP was normal in only 8 cases, but the temperature was below 37.5° C. in every case (table 3). After 7 days the CRP level was normal in all 30 patients tested. The hospital stay lasted 7 days in every case, owing to the use of a standard treatment protocol. No complications, including epiphyseal arrest, were reported during follow-up. None of the patients had a revision procedure.

Discussion

In this study, a new *K. kingae*-specific real-time PCR method was evaluated in a prospective series of consecutive hospitalized children with acute septic arthritis. We also tested, for the first time, blood samples obtained at admission and joint fluid obtained during treatment.

The specificity of the *K. kingae* RT PCR method with a fluorogenic probe was assessed by testing not only pathogens frequently involved in septic arthritis, but also other *Kingella* species, and a phylogenetically related genus. We found that a homologous cpn60 gene is probably shared by *K. kingae, K. oralis* and *K. denitrificans*, and by *Alyssiela* spp. However, one primer pair (Ksm1-2) was highly specific for *K. kingae*. The probe design was based on the sequences of the amplicons obtained with this primer pair and six strains of *K. kingae*, and took into account the presence of several regions bearing point mutations. To further evaluate the specificity of our method, we also tested another primer pair based on the recently sequenced hemolysin gene rtxA [18]. All our real-time PCR-positive samples were also positive for rtxA (not shown) providing evidence of the high specificity of our PCR method.

Thirty-six (40%) of the 89 cases of suspected acute septic arthritis were documented by culture, a proportion consistent with other studies [1-3]. *S. aureus* was the main pathogen detected by culture (19 cases, 53%). *K. kingae* accounted for 19% (7/36) of culture-positive cases, a proportion similar to that reported by Yagupsky et al (22%) [3] and higher than that reported by Luhmann et al (8%) [1]. However, when we added the results of our real-time PCR method, the rate of documented arthritis rose from 40% to 67%, and *K. kingae* became the most prevalent pathogen (31 cases, 52%). In children younger than 24 months, *K. kingae* accounted for 75% (27/36) of the documented cases.

To our knowledge, this is the second study to show the potential benefit of a specific PCR method for the diagnosis of *K. kingae* infections [7]. By comparison with conventional culture, our PCR method increased the *K. kingae* detection rate by a factor of more than four, from 7 to 31 cases. Chometon et al. recently reported that the use of a different specific PCR method increased the number of identified cases of *K. kingae* osteomyelitis and arthritis by a factor of ~2 (from 17 to 39), making this the most prevalent pathogen in children with these diseases [7]. Rosey et al., using a broad-range PCR method, found that 30% of cases of septic arthritis in a pediatric population with a median age of 32 months were due to *K. kingae* [2]. The higher rate observed here (52%) may be due in part to the better sensitivity of specific PCR methods [7].

DNA from *S. pneumoniae* colonizing the throat of young infants can enter the bloodstream and give false-positive diagnosis of infection to this organism using PCR on nucleic acid extraction from blood. [12]. As *K. kingae* colonizes the throat of up to 20% of young infants, Yagupsky et al. pointed out that a positive PCR result for joint fluid might not necessarily prove the responsibility of *K. kingae* [11]. Interestingly, however, we tested presurgical blood samples of 15 patients with a diagnosis of *K. kingae* arthritis, and all were PCR-negative. These results indicate that RT PCR on blood samples does not contribute to the etiological diagnosis, and that PCR positivity of joint fluid is not due to bacterial DNA derived from blood. Therefore we think that we provided a control set which gives evidence of the true benefit of the RT PCR for diagnosis of *K. kingae* arthritis. In addition, RT PCR was always negative in patients with arthritis due to other pathogens, serving also as a control set [11], although they tended to be older than the children with *K. kingae* infection.

The main demographic and clinical characteristics of the 31 cases of acute *K. kingae* arthritis are in keeping with previous reports [6-9, 19-21]. In particular, patients with *K. kingae* infection tended to be young (mean age 19.3 months, versus 98 months for *S. aureus* arthritis, p<0.001), confirming the higher prevalence of this microorganism in children less than 3 years of age [6-9, 19-21]. Clinical and biological signs at admission were often mild, consisting of slightly elevated temperature, CRP and fibrinogen values. Fibrinogen was the most sensitive marker of inflammation in our patients, all of whom had abnormal values. The frequency of *K. kingae* infection was lowest in summer (2 cases), as also noted in previous studies [7, 9, 19]. Again in keeping with the literature, we found that *Kingella* arthritis was always monoarticular, and mainly affected the lower extremities (27/31 cases in our series) [10]. *K. kingae* mainly infected the knee, as expected [10], whereas *S. aureus* or *S. pneumoniae* mainly infected the hip in other series [22, 23]. Indeed in our series *S. aureus* infected the hip in 9 of the 19 cases (not shown).

Lebel et al. suggested that surgical arthrotomy for *K. kingae* arthritis could be postponed if voluntary joint motion and peripheral leukocytosis improved after antibiotic therapy [20]. However, systematic surgery seems preferable in our experience. All our patients had surgical joint lavage in case of purulent joint fluid. When *K. kingae* was isolated, oral antibiotic therapy consisted of amoxicillin alone (150 mg/kg/ 24 h) for 5 weeks. All the patients were cured and were free of sequelae 6 months, probably reflecting the importance of surgical management as well as the low pathogenicity of this bacterium and its high susceptibility to amoxicillin.

One limit of PCR-based diagnosis is that it provides no information on antimicrobial susceptibility. However, *K. kingae* is highly susceptible to β-lactam antibiotics: reported MIC50 values of penicillin G and amoxicillin are 0.023 and 0.16 mg/L [17, 24]. Very few isolates, including three in Iceland, have been reported to produce β-lactamases [25]. Therefore, we believe that, in most countries, a *K. kingae* arthritis diagnosed by PCR may be treated confidently with a β-lactam drug such as amoxicillin, providing an easy switch from intravenous to oral antibiotherapy.

One other advantage of PCR methods is that they can yield an etiological diagnosis several days or weeks after treatment initiation [13-15]. To our knowledge only one study has investigated this property in septic arthritis [16]. Broad-range PCR was applied to serial joint fluid samples from six adults with septic arthritis due to various bacteria. Streptococcus pyogenes, Neisseria meningitis and Peptostreptococcus anaerobius DNA was detected one week after treatment initiation. Likewise, we show here for the first time that *K. kingae* DNA can be detected in joint fluid for up to 6 days after treatment initiation.

In conclusion, our new highly specific RT PCR confirms that *K. kingae* is the major bacterial cause of arthritis in children. We provide strong evidence that *K. kingae* DNA in joint fluids does not arise from nasopharyngeal colonization via the bloodstream, and that the bacterial DNA persists for several days after treatment initiation, allowing retrospective diagnosis. This highly sensitive technique should help to determine in further studies the optimal length of intravenous and oral antibiotic therapy and hospitalization for patients with *K. kingae* arthritis. In a more general consideration our RT PCR may also contribute in the future to the diagnosis of endocarditis, the knowledge on colonisation characteristics of this pathogen and outbreak investigation [4].

REFERENCES

1. Luhmann J D, Luhmann S J. Etiology of septic arthritis in children: an update for the 1990s. Pediatr Emerg Care 1999;15:40-2.
2. Rosey A L, Abachin E, Quesnes G, et al. Development of a broad-range 16S rDNA real-time PCR for the diagnosis of septic arthritis in children. J Microbiol Methods 2007;68: 88-93.
3. Yagupsky P, Dagan R, Howard C W, Einhorn M, Kassis I and Simu A. High prevalence of *Kingella kingae* in joint fluid from children with septic arthritis revealed by the BACTEC blood culture system. J Clin Microbiol 1992;30: 1278-81.
4. Kiang K M, Ogunmodede F, Juni B A, et al. Outbreak of osteomyelitis/septic arthritis caused by *Kingella kingae* among child care center attendees. Pediatrics 2005; 116: e206-13.
5. Yagupsky P, Dagan R, Prajgrod F and Merires M. Respiratory carriage of *Kingella kingae* among healthy children. Pediatr Infect Dis J 1995;14:673-8.
6. Moumile K, Merckx J, Glorion C, Berche P and Ferroni A. Osteoarticular infections caused by *Kingella kingae* in children: contribution of polymerase chain reaction to the microbiologic diagnosis. Pediatr Infect Dis J 2003;22:837-9.
7. Chometon S, Benito Y, Chaker M, et al. Specific real-time polymerase chain reaction places *Kingella kingae* as the most common cause of osteoarticular infections in young children. Pediatr Infect Dis J 2007;26:377-81.
8. Lundy D W, Kehl D K. Increasing prevalence of *Kingella kingae* in osteoarticular infections in young children. J Pediatr Orthop 1998;18:262-7.
9. Verdier I, Gayet-Ageron A, Ploton C, et al. Contribution of a broad range polymerase chain reaction to the diagnosis of osteoarticular infections caused by *Kingella kingae*: description of twenty-four recent pediatric diagnoses. Pediatr Infect Dis J 2005;24:692-6.
10. Yagupsky P. *Kingella kingae*: from medical rarity to an emerging paediatric pathogen. Lancet Infect Dis 2004;4: 358-67.
11. Yagupsky P. Diagnosis of *Kingella kingae* arthritis by polymerase chain reaction analysis. Clin Infect Dis 1999; 29:704-5.
12. Dagan R, Shriker O, Hazan I, et al. Prospective study to determine clinical relevance of detection of pneumococcal DNA in sera of children by PCR. J Clin Microbiol 1998; 36:669-73.
13. Bonacorsi S, Farnoux C, Bidet P, et al. Treatment failure of nosocomial pertussis infection in a very-low-birth-weight neonate. J Clin Microbiol 2006;44:3830-2.
14. Maas K S, Mendez M, Zavaleta M, et al. Evaluation of brucellosis by PCR and persistence after treatment in patients returning to the hospital for follow-up. Am J Trop Med Hyg 2007;76:698-702.
15. Nilsson A C, Bjorkman P and Persson K. Polymerase chain reaction is superior to serology for the diagnosis of acute Mycoplasma pneumoniae infection and reveals a high rate of persistent infection. BMC Microbiol 2008;8: 93.
16. van der Heijden I M, Wilbrink B, Vije A E, Schouls L M, Breedveld F C and Tak P P. Detection of bacterial DNA in serial synovial samples obtained during antibiotic treatment from patients with septic arthritis. Arthritis Rheum 1999;42:2198-203.
17. Yagupsky P, Katz O and Peled N. Antibiotic susceptibility of *Kingella kingae* isolates from respiratory carriers and patients with invasive infections. J Antimicrob Chemother 2001;47:191-3.
18. Kehl-Fie T E, St Geme J W, 3rd. Identification and characterization of an RTX toxin in the emerging pathogen *Kingella kingae*. J Bacteriol 2007;189:430-6.
19. Gene A, Garcia-Garcia J J, Sala P, Sierra M and Huguet R. Enhanced culture detection of *Kingella kingae*, a pathogen of increasing clinical importance in pediatrics. Pediatr Infect Dis J 2004;23:886-8.
20. Lebel E, Rudensky B, Karasik M, Itzchaki M and Schlesinger Y. *Kingella kingae* infections in children. J Pediatr Orthop B 2006;15:289-92.

21. Yagupsky P, Dagan R. *Kingella kingae*: an emerging cause of invasive infections in young children. Clin Infect Dis 1997;24:860-6.
22. Ross J J, Saltzman C L, Carling P and Shapiro D S. Pneumococcal septic arthritis: review of 190 cases. Clin Infect Dis 2003;36:319-27.
23. Wang C L, Wang S M, Yang Y J, Tsai C H and Liu C C. Septic arthritis in children: relationship of causative pathogens, complications, and outcome. J Microbiol Immunol Infect 2003;36:41-6.
24. Kugler K C, Biedenbach D J and Jones R N. Determination of the antimicrobial activity of 29 clinically important compounds tested against fastidious HACEK group organisms. Diagn Microbiol Infect Dis 1999;34:73-6.
25. Birgisson H, Steingrimsson O and Gudnason T. *Kingella kingae* infections in paediatric patients: 5 cases of septic arthritis, osteomyelitis and bacteraemia. Scand J Infect Dis 1997;29:495-8.

TABLE 1

Primer specificity for *K. kingae* DNA amplification

| | | Amplification with primers[a] | |
|---|---|---|---|
| Species | Origin | KingF-R | Ksm1-2 |
| *Kingella kingae* | CIP 80.16 | + | + |
| *Kingella kingae* | CIP 68.12 | + | + |
| *Kingella kingae* | CIP 73.01 | + | + |
| *Kingella kingae* | CIP 102470 | + | + |
| *Kingella denitrificans* | CIP 103473 | + | − |
| *Kingella oralis* | CIP 103803 | + | − |
| *Capnocytophaga canimorsus* | CIP 103936 | − | − |
| *Capnocytophaga ochracea* | CIP 103448 | − | − |
| *Aggregatibacter actinomycetemcomitans* | CIP 52.106 | n.s. band | − |
| *Aggregatibacter aphrophilus* | CIP 70.73 | − | − |
| *Haemophilus influenzae* | CIP 52.152 | − | − |
| *Cardiobacterium hominis* | CIP 70.70 | − | − |
| *Eikenella corrodens* | CIP 70.75 | n.s. band | − |
| *Neisseria polysaccharea* | CIP 100113 | − | − |
| *Alysiella crassa* | CIP 103341 | + | − |
| *Conchiformibius steedae* | CIP 103435 | − | − |
| *Neisseria meningitidis* W135 | Clinical isolate | − | − |
| *Streptococcus pneumoniae* | Clinical isolate | − | − |
| *Streptococcus pyogenes* | Clinical isolate | − | − |
| *Staphylococcus aureus* | Clinical isolate | − | − |

[a] +, positive amplification with a band of the expected length; −, no band observed, n.s. band: non specific band (of unexpected length).

TABLE 2

Microbiological diagnosis of 31 pediatric cases of acute *Kingella kingae* arthritis

| Diagnostic method | Proportions (%) of positive results |
|---|---|
| Cultures of joint fluid on solid media | 3/31 (10) |
| Cultures of joint fluid in blood culture vials | 7/31 (22) |
| Peripheral blood culture | 0/31 |
| Real-time PCR on joint fluid at admission | 31/31 (100) |
| Real-time PCR on blood samples at admission | 0/15 |
| Real-time PCR on joint drainage fluid | |
| 2 days after treatment initiation | 9/9 (100) |
| 4 days after treatment initiation | 4/5 (80) |
| 6 days after treatment initiation | 3/4 (75) |

TABLE 3

Clinical and biological characteristics of 31 pediatric cases of acute *Kingella kingae* arthritis

| Characteristics | Patients (%) | Median/mean | 10$^{th}$-90$^{th}$ percentiles | range |
|---|---|---|---|---|
| Age (months) | | 16/19.3 | 10-38 | 8-68 |
| Boys | 18/31 (58) | | | |
| Locations | | | | |
| Knee | 16/31 (52) | | | |
| Hip | 8/31 (26) | | | |
| Ankle | 3/31 (10) | | | |
| Shoulder | 1/31 (3) | | | |
| Elbow | 1/31 (3) | | | |
| Wrist | 1/31 (3) | | | |
| Proximal interphalangeal joint | 1/31 (3) | | | |
| Temperature at admission (° C.) | 19/31 (61)[b] | 38/38 | 37-38.8 | 36.3-39.9 |
| Temperature on day 3 | 0/31 (0)[b] | | | |
| CRP (mg/l) at admission | 30/31 (97)[b] | 32/39 | 18-69 | 10-133 |
| CRP on day 3 | 23/31 (74)[b] | 22/28 | 10-63 | 10-122 |
| CRP on day 7 | 0/30 (0)[b] | | | |
| WBC[a] (×1000/mm3) at admission | 3/31 (10)[b] | 12.3/12.4 | 9.3-16.3 | 6-19.6 |
| Fibrinogen (g/l) at admission | 27/27 (100)[b] | 5.4/5.8 | 5-7.1 | 4.2-9.1 |

[a] WBC; white blood cell count.
[b] proportion of abnormal values (Temperature ≥38° C., CRP >10 mg/l, WBC >17000/mm³ between 6 months and 2 years; >15000/mm³ between 4 and 6 years, fibrinogen >4 g/l

The invention claimed is:

1. A method for detecting the presence of *Kingella kingae* in a biological sample of a patient, comprising amplifying part of a chaperonin gene of a microorganism of *Kingella* genus in a biological sample of a patient; and detecting the presence of amplified chaperonin gene, wherein the presence of amplified chaperonin gene is indicative of *Kingella kingae* in said biological sample, wherein said chaperonin gene is cpn60, a partial sequence of which being represented by SEQ ID NO: 1, and wherein said amplification is performed with the pair of primers SEQ ID NO: 2 and SEQ ID NO: 3.

2. The method of claim 1, wherein the amplified sequence comprises nucleotides 225 to 399 of SEQ ID NO: 1.

3. The method of claim 1, wherein said biological sample is a joint fluid sample.

4. The method of claim 1, wherein said patient is a child less than 15 years old.

5. The method of claim 1, wherein said patient has acute arthritis.

6. The method of claim 1, wherein said patient has endocarditis.

7. The method of claim 1, wherein said amplification is real-time PCR.

8. The method of claim 1, wherein detection of the amplification product is performed with a probe of SEQ ID NO: 7.

9. The method of claim 8, wherein said probe contains 6-carboxyfluorescein at its 5' end and black hole quencher at its 3' end.

\* \* \* \* \*

SEQUENCE LISTING

```
<160> NUMBER OF SEQ ID NOS: 17

<210> SEQ ID NO 1
<211> LENGTH: 555
<212> TYPE: DNA
<213> ORGANISM: Kingella kingae

<400> SEQUENCE: 1
gcaaccgtgt tggcgcaagc gattgttgct gaaggcatga aatacgttac cgcaggcatg      60
aatcctaccg atttgaaacg cggtattgac aaagcagtgg cggctttggt tggcgaattg     120
gcaaacatcg cgaaaccttg cgaaacatac gagcaaatcg ctcaagtggg cgcgatttct     180
```

```
gcgaactctg acgagcaagt tggcaaaatc attgcagacg cgatgcaaga agtcggcaaa      240
gagggcgtga ttaccgttga agacggcaaa tcattggaaa acgagttaga agtggttaaa      300
ggtatgcaat ttgaccgtgg ctacttgtcg ccttatttcg tgaatgattt ggaaaaacaa      360
atcgctggtt tggacagccc atttgtgttg ttgtttgaca aaaaaatcag caatatccgt      420
gatttgttgc ccgttttgga acaagtggca aaaccagcc gcccattgtt gattatcgcg       480
gaagacgtgg aaggcgaagc attggcaact ttggttgtaa acagcattcg cggtatttg      540 aaaaccgttg cggta                                                       555

<210> SEQ ID NO 2
<211> LENGTH: 19
<212> TYPE: DNA
<213> ORGANISM: Artificial
<220> FEATURE:
<223> OTHER INFORMATION: Synthetic primer Ksm1

<400> SEQUENCE: 2
gcaagaagtc ggcaaagag                                                    19

<210> SEQ ID NO 3
<211> LENGTH: 22
<212> TYPE: DNA
<213> ORGANISM: Artificial
<220> FEATURE:
<223> OTHER INFORMATION: Synthetic primer Ksm2

<400> SEQUENCE: 3
gtcaaacaac aacacaaatg gg                                                22

<210> SEQ ID NO 4
<211> LENGTH: 24
<212> TYPE: DNA
<213> ORGANISM: Artificial
<220> FEATURE:
<223> OTHER INFORMATION: Synthetic primer KingF

<400> SEQUENCE: 4
tgttggcgca agcgattgtt gctg                                              24

<210> SEQ ID NO 5
<211> LENGTH: 23
<212> TYPE: DNA
<213> ORGANISM: Artificial
<220> FEATURE:
<223> OTHER INFORMATION: Synthetic primer KingR

<400> SEQUENCE: 5
cgcccacttg agcgatttgc tcg                                               23

<210> SEQ ID NO 6
<211> LENGTH: 35
<212> TYPE: DNA
<213> ORGANISM: Artificial
<220> FEATURE:
<223> OTHER INFORMATION: Synthetic probe

<400> SEQUENCE: 6
cgcgatcgcg acaagtagcc acggtcaaga tcgcg                                  35

<210> SEQ ID NO 7
<211> LENGTH: 36
<212> TYPE: DNA
<213> ORGANISM: Artificial
<220> FEATURE:
```

```
<223> OTHER INFORMATION: Synthetic probe

<400> SEQUENCE: 7
cggtcaaatt gcatacctt aaccacttct tgaccg                                36

<210> SEQ ID NO 8
<211> LENGTH: 21
<212> TYPE: DNA
<213> ORGANISM: Artificial
<220> FEATURE:
<223> OTHER INFORMATION: Synthetic primer B2M-TR-1

<400> SEQUENCE: 8
gcaaggactg gtctttctat c                                               21

<210> SEQ ID NO 9
<211> LENGTH: 23
<212> TYPE: DNA
<213> ORGANISM: Artificial
<220> FEATURE:
<223> OTHER INFORMATION: Synthetic primer B2M-TR-2

<400> SEQUENCE: 9
tacacaactt tcagcagctt aca                                             23

<210> SEQ ID NO 10
<211> LENGTH: 36
<212> TYPE: DNA
<213> ORGANISM: Artificial
<220> FEATURE:
<223> OTHER INFORMATION: Synthetic probe

<400> SEQUENCE: 10
cgtgccctgc cgtgtgaacc atgtgacttt ggcacg                               36

<210> SEQ ID NO 11
<211> LENGTH: 175
<212> TYPE: DNA
<213> ORGANISM: Kingella kingae

<400> SEQUENCE: 11
gcaagaagtc ggcaaagagg gcgtgattac cgttgaaggc ggcaaatcat tggaaaacga     60
gttagaagtg gttaaaggta tgcaatttga ccgtggctac ttgtcgcctt atttcgtgaa    120
tgatttggaa aaacaaatcg ctggtttgga cagcccattt gtgttgttgt ttgac         175

<210> SEQ ID NO 12
<211> LENGTH: 175
<212> TYPE: DNA
<213> ORGANISM: Kingella kingae

<400> SEQUENCE: 12
gcaagaagtc ggcaaagagg gcgtgatttc ccttgaaaac ggcaaatcat tggaaaacga     60
gttggaagtg gttaaaggta tgcaatttga ccgtggctac ttgtcgcctt atttcgtgaa    120
tgatttggaa aaacaaatcg ctggtttgga cagcccattt gtgttgttgt ttgac         175

<210> SEQ ID NO 13
<211> LENGTH: 175
<212> TYPE: DNA
<213> ORGANISM: Kingella kingae

<400> SEQUENCE: 13
gcaagaagtc ggcaaagagg gcgtgattac cgttgaaggc ggcaaatcat tggaaaacga     60
```

```
gttggaagtg gttaaaggta tgcaatttga ccgtggctac ttgtcgcctt atttcgtgaa      120
tgatttggaa aaacaaatcg ctggtttgga cagcccattt gtgttgttgt ttgac           175

<210> SEQ ID NO 14
<211> LENGTH: 175
<212> TYPE: DNA
<213> ORGANISM: Kingella kingae

<400> SEQUENCE: 14
gcaagaagtc ggcaaagagg gcgtgattac cgttgaagac ggcaaatcat tggaaaacga      60
gttggaagtg gttaaaggta tgcaatttga ccgcggctac ttgtcacctt attttgtgaa     120
tgatttggaa aaacaaatcg ctggtttgga cagcccattt gtgttgttgt ttgac           175

<210> SEQ ID NO 15
<211> LENGTH: 143
<212> TYPE: DNA
<213> ORGANISM: Kingella kingae

<400> SEQUENCE: 15
gcaagaagtc ggcaaagagg gcgtgattac cgttgaagac ggcaaatcat tggaaaacga      60
gttggaagtg gttaaaggta tgcaatttga ccgcggctac ttgtcacctt attttgtgaa     120
tgatttggaa aaacaaatcg ctg                                             143

<210> SEQ ID NO 16
<211> LENGTH: 143
<212> TYPE: DNA
<213> ORGANISM: Kingella kingae

<400> SEQUENCE: 16
gcaagaagtc ggcaaagagg gcgtgattac cgttgaagac ggcaaatcat tggaaaacga      60
gttggaagtg gttaaaggta tgcaatttga ccgcggctac ttgtcacctt attttgtgaa     120
tgatttggaa aaacaaatcg ctg                                             143

<210> SEQ ID NO 17
<211> LENGTH: 175
<212> TYPE: DNA
<213> ORGANISM: Artificial
<220> FEATURE:
<223> OTHER INFORMATION: Synthetic consensus sequence

<400> SEQUENCE: 17
gcaagaagtc ggcaaagagg gcgtgattwc csttgaarrc ggcaaatcat tggaaaacga      60
gttrgaagtg gttaaaggta tgcaatttga ccgyggctac ttgtcrcctt atttygtgaa     120
tgatttggaa aaacaaatcg ctggtttgga cagcccattt gtgttgttgt ttgac           175
```